United States Patent [19]

Nguyen

[11] Patent Number: 5,175,046
[45] Date of Patent: Dec. 29, 1992

[54] SUPERABSORBENT LAMINATE STRUCTURE

[75] Inventor: Hien V. Nguyen, East Windsor, N.J.

[73] Assignee: Chicopee, New Brunswick, N.J.

[21] Appl. No.: 664,165

[22] Filed: Mar. 4, 1991

[51] Int. Cl.⁵ .......................................... B32B 27/14
[52] U.S. Cl. ...................................... 428/198; 428/68; 428/74; 428/283; 428/284; 428/317.9; 428/323; 428/327
[58] Field of Search .............. 428/283, 284, 317.9, 428/323, 327, 68, 195, 198, 201, 206, 74

[56] References Cited

U.S. PATENT DOCUMENTS

| | | | |
|---|---|---|---|
| 4,381,782 | 5/1983 | Mazurak et al. | 428/283 |
| 4,578,068 | 3/1986 | Kramer et al. | 428/283 |
| 4,699,823 | 10/1987 | Hellenberger et al. | 428/283 |
| 4,758,466 | 7/1988 | Dabi et al. | 428/283 |
| 4,851,069 | 7/1989 | Packard et al. | 428/327 |
| 4,861,652 | 8/1989 | Luppert et al. | 428/284 |
| 4,888,231 | 12/1989 | Angstadt | 428/283 |
| 4,902,565 | 2/1990 | Brook | 428/284 |
| 4,994,053 | 2/1991 | Lang | 428/913 |
| 5,041,104 | 8/1991 | Seal | 428/283 |
| 5,128,193 | 7/1992 | Anapol et al. | 428/283 |

Primary Examiner—James J. Bell
Attorney, Agent, or Firm—Lawrence D. Schuler

[57] ABSTRACT

A laminated structure in which a superabsorbent material is provided as a layer of discrete discontinuous chunks or elements attached to a continuous porous support layer. The superabsorbent element is provided by saturating a porous substrate with an acrylic acid monomer solution, polymerizing and crosslinking the monomer in the web, and then dicing the monomer/web substrate to produce discrete superabsorbent elements. The superabsorbent elements having various shaped are then affixed to the flexible porous support layer by friction so as to provide the flexible superabsorbent laminated structure.

12 Claims, 1 Drawing Sheet

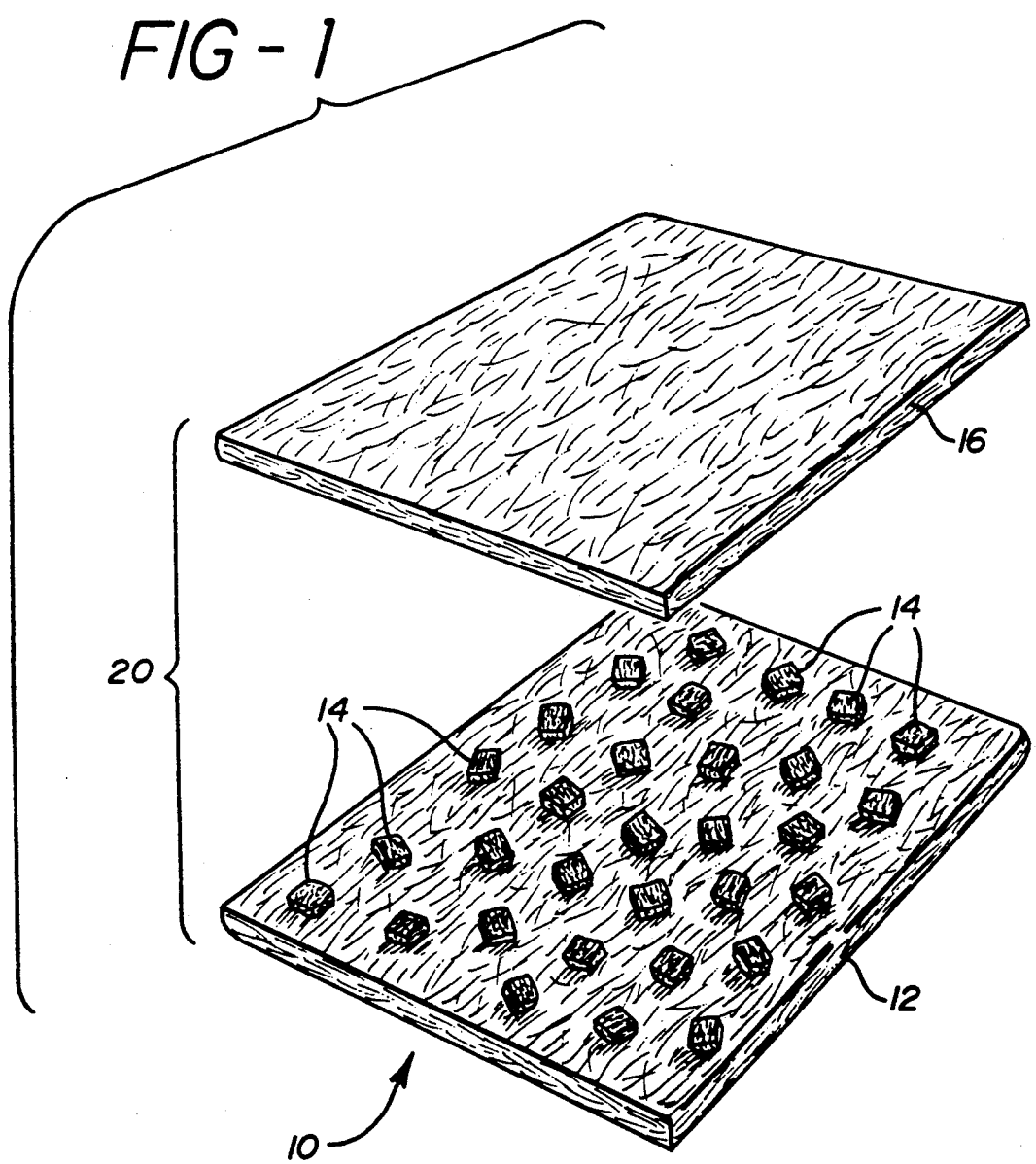

SUPERABSORBENT LAMINATE STRUCTURE

BACKGROUND OF THE INVENTION

This invention relates to improved flexible laminated structures having superabsorbent material incorporated therein. It relates particularly to laminated structures in which the superabsorbent material is provided as discrete chunks or pieces of superabsorbent element frictionally secured to a porous support layer.

Commercial superabsorbent materials most often are provided in the form of fine powders which have been incorporated into absorbent fibrous webs, as disclosed by U.S. Pat. No. 4,500,315 to Pieniak et al. However, it has been found that when such powders are incorporated in a fibrous web, they tend to sift out of the web during handling. On the other hand, superabsorbent materials provided in the form of continuous film or sheets, tend to be undesirably stiff and difficult to use in absorbent products. A variation on the use of films is to spread superabsorbent material on the surface of a porous material such as a fiber web, but the resulting web is also very stiff. Thus, it would be desirable to provide an absorbent structure containing superabsorbent material which overcomes both of these problems. These disadvantages of the prior art absorbent web structures have led to the development of the improved superabsorbent laminated structure of the present invention, in which superabsorbent material is provided as discrete elements frictionally attached to a flexible porous support layer.

THE PRIOR ART

One of the earliest patents showing the use of superabsorbent in a fibrous structure is U.S. Pat. No. 3,670,731. In this disclosure, the superabsorbent is not fixed in the structure and dusting of the superabsorbent out of the structure prevails. Also, the superabsorbent agglomerates within the structure and would suffer from gel blocking thus greatly reducing the effectiveness of the superabsorbent. Gel blocking is the phenomenon which occurs when on the introduction of a liquid the outside particles of an agglomeration of particles is wetted and swells and effectively blocks off the flow of liquid to the more internal particles of the agglomeration. Since the internal or blocked particles cannot absorb liquid the overall effect is a reduced absorbency as compared to the potential absorbency if all the particles could absorb to their full potential and hence a reduced efficacy of the superabsorbent polymer system.

U.S. Pat. No. 4,443,492, discloses a method of improving the absorbency rate of a superabsorbent which comprises wetting an in-situ polymerized superabsorbent and thereafter drying the wet material.

Canadian Patent 1,163,599 discloses a method by which superabsorbent is formed in-situ in a fibrous web. The product of Canadian 1,163,599 can serve as a starting material for the present invention.

In U.S. Pat. No. 4,354,487, a superabsorbent is attached by in-situ polymerization to individual fibers of a fibrous web. The superabsorbent containing fibrous web is then subjected to a mechanical treatment in which the fibers are separated and individualized. The resulting product has reduced stiffness and the superabsorbent therein has a reduced tendency to sift out of the fibrous web.

Another example of a web comprising a superabsorbent material is disclosed in U.S. Pat. No. 4,500,315. A water mist and compressive pressure are employed to anchor the superabsorbent in the web. Such a web tends to be undesirably stiff and is prone to dusting out of the superabsorbent material.

SUMMARY OF THE INVENTION

In accordance with the present invention there is provided an improved superabsorbent laminated structure which comprises a porous support layer with discrete superabsorbent elements attached thereto in a discontinuous pattern. The support layer remains soft and pliable and the discrete superabsorbent elements do not move or sift out of the laminated structure. The laminated structure, according to the invention, comprises a continuous porous support layer and a discontinuous element which comprises finite chunks or pieces of porous substrate containing superabsorbent polymer. The discrete superabsorbent elements are frictionally attached to the porous support layer.

More specifically, the superabsorbent laminated structure comprises two layers including a continuous phase serving as a support layer and a discontinuous phase containing superabsorbent elements serving as an improved absorber and immobilizer of liquids. Preferably the support layer also serves as a wicking layer.

The support layer comprises a pliable porous material such as a foam, tissue, or fibrous web. The fibrous web can be fluffy or compressed, it can be unbonded or bonded by chemical or thermal means, or it can be hydrogen bonded such as paper. The fibers of the support layer can be short, as in the case of wood pulp or synthetic pulp fibers or long as in the case of cotton or staple length synthetic fibers.

The superabsorbent elements are in the form of small sheets, or blocks/chunks of materials having a size of from about 1 mm to about 1 cm in their longest dimension. The superabsorbent elements may be of any convenient or desired shape.

The superabsorbent elements are porous structures (fibrous or foam-like) with superabsorbent material as the major or only added component. The superabsorbent elements maybe obtained, e.g. by chopping, from the superabsorbent-coated fiber webs described in Canadian Patent 1,163,599, the teachings of which are incorporated herein by reference. The substrate material can be an open cell foam matrix or any similar material that will frictionally engage with the support layer under the influence of a compressive force.

Any superabsorbent polymer may be used in the superabsorbent element of the present invention. The term "superabsorbent polymer" means a water insoluble, water swellable material which absorbs and is capable of holding at least about ten times its own weight of water or aqueous fluid.

These superabsorbent elements maybe formed by coating a hydrophilic monomer such as neutralized acrylic acid onto a substrate material such as a fibrous web, pulp web, or foam material, and then causing the monomer to be crosslinked through the application of electron beam irradiation, heat, chemical agents, etc. A process for preparing the superabsorbent containing fibrous web is disclosed in Canadian Patent 1,163,599. A irradiated superabsorbent-containing fibrous web is then chopped up into small bits and pieces to provide the superabsorbent elements. The superabsorbent elements may also be prepared by substantially uniformly applying commercially available superabsorbent powders to premoistened substrate with subsequent drying of the structure. The moisture causes the powder to partially swell and to become tacky so that on drying the superabsorbent sticks or is anchored to the substrate and hence is made immobile and prevented from dusting out of the structure during processing or use.

The superabsorbent elements comprising the laminated structure can be substantially identical in size and shape but will usually have different and random sizes and shapes.

As mentioned earlier herein, the discrete superabsorbent elements are attached to the support layer in a discontinuous pattern, i.e. some space is left between adjacent individual superabsorbent elements. The superabsorbent elements may be disposed on the support layer either randomly or in a regular pattern.

The superabsorbent elements may cover as little as about 5% of the support layer or as much as about 75%. Preferably, the surface coverage is 40%–60%. The super-absorbent elements are anchored to the support layer by frictional engagement and entanglement of fibers brought about by compression. A compressive force of about 300 lbs/sq. in. to about 5,000 lbs/sq. in. is usually required to anchor the superabsorbent substrates to the support layer.

If desired, the superabsorbent elements can be sandwiched between two fibrous layers. Due to the discontinuity of the superabsorbent element, the laminated structure as a whole is flexible and pliable. Since the superabsorbent elements comprising the superabsorbent polymer attached to the fibrous substrate material are anchored well to the support layer, there is no moving or dusting out of the superabsorbent polymer from the laminated structure.

Advantages of this invention are that the laminated structure is flexible and pliable because the superabsorbent elements are provided in a discontinuous pattern on the support layer. The superabsorbent elements are porous structures which facilitate the accessibility to liquid to be absorbed. Due to their porous nature and the compressive force used during preparation of the laminated structure, the superabsorbent elements are well anchored to the support layer so that undesired dusting out and loss of superabsorbent polymer from the laminated structure is substantially avoided.

The laminated structure of this invention finds use as an absorbent element in disposable diapers, sanitary napkins, incontinent pads, wipes, and the like.

BRIEF DESCRIPTION OF THE DRAWINGS

FIG. 1 shows a perspective view of the superabsorbent laminated structure according to the invention in which pieces of superabsorbent elements are enclosed between a porous support layer and a porous cover layer.

DESCRIPTION OF INVENTION

As shown in FIG. 1, the laminated structure 10 comprises a support layer 12 onto which is compressively attached discrete chunks or pieces of a superabsorbent elements 14. These superabsorbent elements 14 are porous structures comprising a substrate material and a superabsorbent polymer. The superabsorbent elements are provided as a discontinuous layer frictionally attached to support layer 12 which optionally also serves as a wicking layer. The discrete superabsorbent elements 14 are attached to support/layer 12 by frictional engagement.

A cover layer 16 of (e.g.) porous nonwoven material is preferably placed over the laminated structure 10. Cover layer 16 and laminated structure 10 may be passed through a pair of rollers to provide composite absorbent structure 20. Cover layer 16 can be the same as support layer 12 or it can be a different material having different liquid wicking characteristics as desired.

The invention will be further described by reference to the following examples which should not be regarded as limiting in scope.

EXAMPLE 1

The substrate material used for forming the superabsorbent elements is a pulp web made of a Southern pine wood and having 130 $g/m^2$ density. This pulp web is saturated with a solution of acrylic acid monomer 85% neutralized by sodium hydroxide and 15% neutralized by potassium carbonate and diluted to 42 wt % monomer concentration. Excess monomer solution is removed by passing the saturated substrate over a vacuum suction slot. This now porous monomer-treated substrate is irradiated by an electron beam dose which causes polymerization and crosslinking of the monomer and results in a superabsorbent coated pulp web substrate. The superabsorbent add-on level, i.e. weight of superabsorbent polymer added per weight of substrate, is about 200 wt %. The coated web substrate is again coated with the monomer solution by repeating the steps above which brings the superabsorbent add-on level to 400 wt %.

The superabsorbent coated substrate is then swollen in water and dried. This pre-swelling step is preferred but not necessary and increases the porosity of the superabsorbent-coated web and lessens the swelling constraints of the superabsorbent polymer. This pre-swelling step improves the absorbency of the superabsorbent-coated web material so that it has an absorption value of 15.7 g saline solution/g substrate material as compared to 10 g/g for a non-pre-swelled substrate. The superabsorbent-coated web substrate is then diced in pieces of more or less irregular shapes and sizes to form the superabsorbent elements. The superabsorbent elements are placed between two pulp support webs and the laminate is compressed at 300 psi pressure to form the final laminated structure product of the invention. This procedure produces a soft and pliable pulp laminate web structure containing an increased amount of superabsorbent material which does not dust from the structure.

EXAMPLE 2

The same procedure is used as in Example 1 except the superabsorbent elements are anchored onto one or two layers of tissue paper. If desired, a more fluffy web such as pulp can be used to cover the superabsorbent tissue paper to form a complete superabsorbent laminated structure.

EXAMPLE 3

Variations of Example 1 are produced using mixtures of chemical pulp and thermo-mechanical pulp as the substrate material. The weight of the webs is 70 $g/m^2$, the monomer solution is the same as in Example 1 and the polymer add-on level is 160–200 wt %. The absorbency of the superabsorbent elements is 8–9.1 g/saline solution/g of superabsorbent element for non-pre-swollen samples and is 11.9–12.7 g solution/g of superabsorbent element for pre-swollen samples.

EXAMPLE 4

A variation of Example 2 uses a high denier, high bulk recovery polyester fiber web as the skeleton material for the substrate material. The web fiber size is on the order of six denier, the monomer solution used to make superabsorbent elements is partially neutralized by potassium hydroxide (KOH) and the monomer concentration is about 65 wt %. The superabsorbent polymer add-on level is about 1,000 wt %. The absorbency of the superabsorbent elements is around 9 g/saline solution/g of element.

What is claimed is:

1. A laminated structure comprising a porous support layer and discrete superabsorbent elements frictionally secured to said support layer in a discontinuous pattern, said superabsorbent elements comprising a superabsorbent polymer and a substrate material.

2. The laminated structure of claim 1 further comprising a porous cover layer, said cover layer being placed so that said superabsorbent elements are located between said support layer and said cover layer.

3. The laminated structure of claim 1 wherein said support layer is a layer of tissue.

4. The laminated structure of claim 1 wherein said support layer is a fibrous web.

5. The laminated structure of claim 1 wherein said support layer is an open-cell foam.

6. The laminated structure of claim 1 wherein said substrate material is a fibrous web.

7. The laminated structure of claim 1 wherein said substrate material is an open-cell foam.

8. The laminated structure of claim 1 wherein said substrate material is a tissue web.

9. The laminated structure of claim 1 wherein said superabsorbent elements cover from 5% to 75% of the surface area of said supporting layer.

10. The laminated structure of claim 1 wherein said superabsorbent polymer is water insoluble, water swellable, and capable of absorbing at least ten times its own weight of water.

11. The laminated structure of claim 1 wherein said superabsorbent elements have a size of about 1 mm to about 1 cm.

12. The laminated structure of claim 1 wherein said superabsorbent elements consist of polymerized monomer coated substrate having a polymer add-on level of at least about 100 wt %.

* * * * *